United States Patent [19]

Hakki

[11] Patent Number: 5,188,592
[45] Date of Patent: Feb. 23, 1993

[54] DYNAMIC PRESSURIZED CATHETER WITH SIMULTANEOUS OXYGEN DELIVERY AND SUCTION

[76] Inventor: Sam I. Hakki, 8601 State Rd. 39 North, Plant City, Fla. 33565

[21] Appl. No.: 719,479

[22] Filed: Jun. 24, 1991

[51] Int. Cl.5 .............................................. A61M 1/00
[52] U.S. Cl. ...................................... 604/35; 604/28; 604/43; 604/96
[58] Field of Search ...................... 604/27, 28, 30, 35, 604/32, 33, 39, 45, 43, 96, 97, 98, 99, 102

[56] References Cited

U.S. PATENT DOCUMENTS

| | | | |
|---|---|---|---|
| 3,999,554 | 12/1976 | Kim et al. | 604/45 |
| 4,041,936 | 8/1977 | Carden. | |
| 4,244,362 | 1/1981 | Anderson. | |
| 4,300,550 | 11/1981 | Gandi et al. | 604/35 |
| 4,327,720 | 5/1982 | Bronson et al. | |
| 4,356,824 | 11/1982 | Vazquez | 604/35 |
| 4,364,394 | 12/1982 | Wilkinson | 604/35 |
| 4,468,216 | 8/1984 | Muto. | |
| 4,607,635 | 8/1986 | Heyden | 604/35 |
| 4,637,389 | 1/1987 | Heyden | 604/43 |
| 4,642,092 | 2/1987 | Moss | 604/43 |
| 4,737,147 | 4/1988 | Ferrando et al. | 604/43 |
| 4,781,677 | 11/1988 | Wilcox | 604/28 |
| 4,790,812 | 12/1988 | Hawkins et al. | 604/43 |
| 4,840,173 | 2/1989 | Porter. | |
| 4,906,238 | 3/1990 | Greenfeld | 604/43 |

FOREIGN PATENT DOCUMENTS 0044804  1/1982  European Pat. Off. ............ 604/43

Primary Examiner—Paul J. Hirsch
Attorney, Agent, or Firm—Frijouf, Rust & Pyle

[57] ABSTRACT

An apparatus and method is disclosed for an improved multi-tubed catheter for physically dislodging and removing material from a lung by suction and simultaneously aerating the lung with oxygen. The catheter comprises an oxygen tube for conveying oxygen into the lung, a suction tube adapted to remove material from the lung and an inflation tube for inflating a small balloon for separating the flow of oxygen from the suction. As the multi-tubed catheter is moved through the lung, the balloon mechanically dislodges material from the lung to be conveyed out of the lung through the suction tube. The lung is contiuously ventilated by oxygen during the removal process.

13 Claims, 3 Drawing Sheets

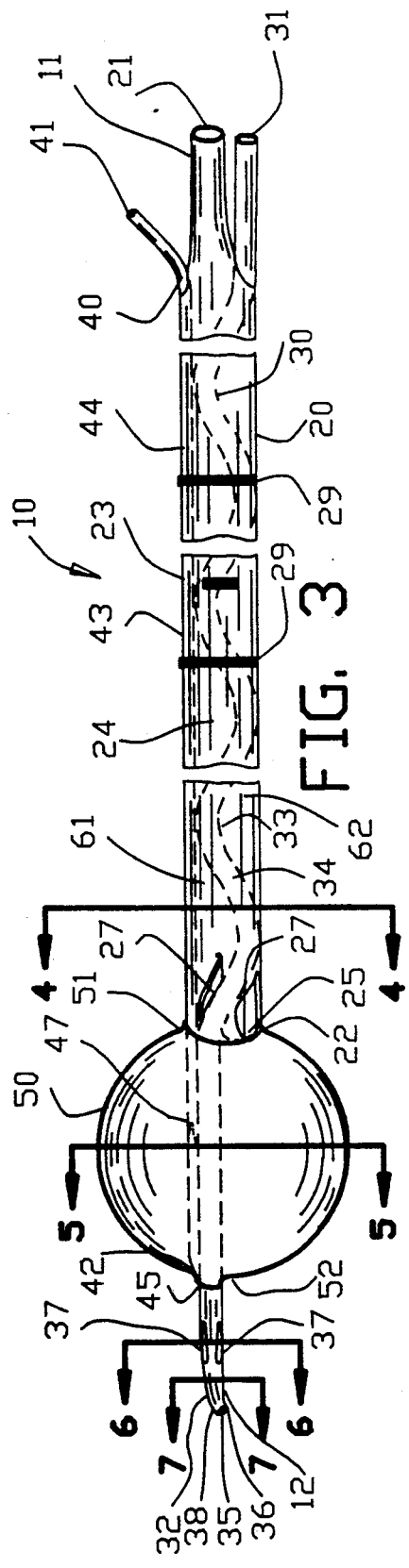
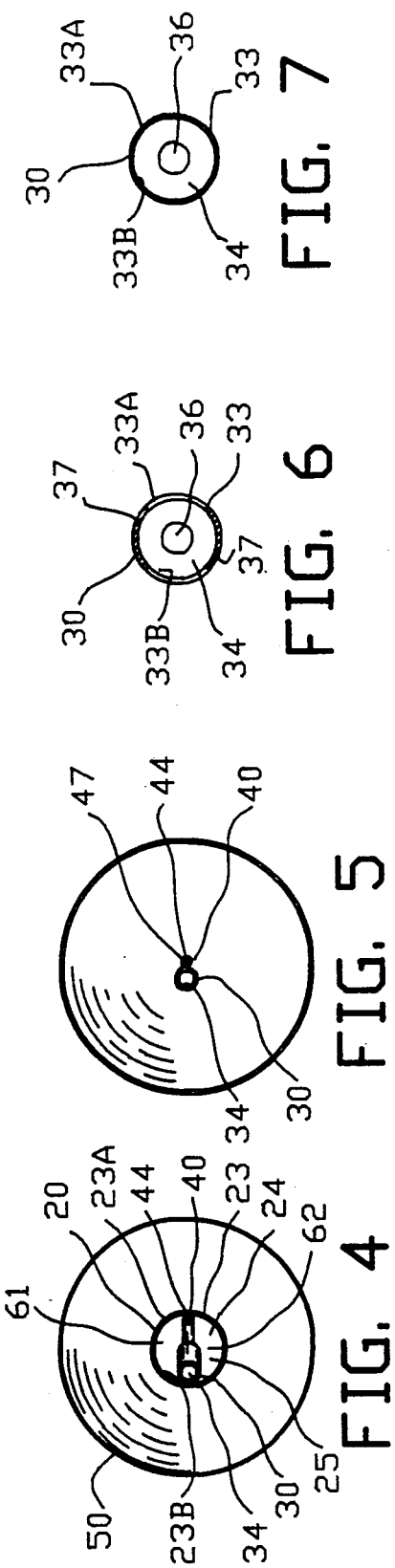

DYNAMIC PRESSURIZED CATHETER WITH SIMULTANEOUS OXYGEN DELIVERY AND SUCTION

BACKGROUND OF THE INVENTION

1. Field Of The Invention

This invention relates to a catheter, and more particularly to an endotracheal bronchial suction catheter, that simultaneously removes material from the respiratory tract of a patient and supplies oxygen to a patient.

2. Background Problem and Prior Art

In a number of medical situations, including routine surgery and intensive care, the breathing of a patient is assisted by artificial means such as a mechanical ventilator. When a mechanical ventilator is in use, air is forced into the lungs through the trachea via an endotracheal tube (ETT). The endotracheal tube (ETT) is inserted through the nose or mouth into the trachea of the patient so that a distal tip of the endotracheal tube (ETT) extends beyond the vocal cords of the patient. When the patient is being assisted by a mechanical ventilator through an endotracheal tube (ETT), the patient is referred to as being intubated or ventilated.

The lungs and trachea of a person produce mucus continuously. Normally, the mucus of the respiratory tract is cleared from the airways by natural means such as coughing. However, an intubated patient has no means by which to clear the respiratory tract of mucus, particularly if the patient is confined to a bed or the patient is unconscious. Over time, mucus or other fluids collect in the airways of an intubated patient which interferes with the oxygen exchange in the lungs of the intubated patient. Accordingly, the mucus or the other fluids must be periodically suctioned out of the lungs of the intubated patient.

In treatment situations where a solid or a fluid material, such as mucus, must be removed from a bronchial cavities or respiratory tract of a patient, a problem arises of supplying the patient with oxygen while the solid or the fluid material is being removed by suction. Typically, a single hollow tube is inserted down the trachea of the patient and is directed into a selected bronchus. The single hollow tube may be used sequentially for two distinct and separate functions. First, the single hollow tube is connected to a source of vacuum to remove the solid or the fluid material by suction from the lungs of the patient. Second, the single hollow tube is connected to a source of pressurized oxygen to conduct an oxygen-rich gas into the lung so that the patient may be supplied with oxygen for respiration.

When a single tube is used sequentially, the tube is timeshared. When a single tube is timeshared, the tube is used alternately connected to the source of vacuum or the source of pressurized oxygen for alternately withdrawing the solid or the fluid material from the lungs of the patient or for supplying the patient with oxygen for respiration. The alternation between the source of vacuum and the source of pressurized oxygen may be accomplished by a human operator or assisted by a mechanical device.

Obviously, there are disadvantages associated with the alternate use of a single tube withdrawing the solid or the fluid material from the lungs of the patient or for supplying the patient with oxygen for respiration. First, pressurized oxygen cannot be supplied to the patient until the single tube is cleared of all of the solid or the fluid material removed from the lungs or the pressurized oxygen will push the solid or the fluid material back into the lung. Second, the pressurized oxygen may serve to undo the cleaning done by the previous vacuum suction. Third, the periods in which no oxygen is being supplied to the patient could be detrimental and may cause hypoxia and the consequences thereof.

Heretofore, there have been a number of mechanical devices concerned with the problems of endotracheal intubation and the removal of material from the respiratory tract.

U.S. Pat. No. 4,468,216 to Muto describes an irrigation suction catheter which can be inserted into either a trachea or an esophagus of the patient. The distal tip of the catheter comprises an irrigation tube disposed within a suction tube. A fluid such as saline solution is emitted from the irrigation tube to dislodge particles while the dislodged particles are removed by the suction tube.

U.S. Pat. No. 4,327,720 to Bronson et al. discloses a device for accessing the trachea of a patient enabling the insertion of a suction tube or a fiber-optic scope. The device is primarily concerned with rectifying a common problem of accidentally inserting the suction tube or the fiber-optic scope within the esophagus instead of the trachea or vice-versa.

U.S. Pat. No. 4,041,936 to Carden discloses a device for insertion into the respiratory tract of a patient to give access to a fiber-optic scope (FOS). A tube and a tip of the device is adapted to allow forced-air ventilation of the lung during the examination of the respiratory tract of the patient. The tip of the tube comprises an inflatable cuff by which a portion of the respiratory tract may be sealed off and pressurized. Although the provides a means for visually inspecting the lung, the device is not designed for routinely removing materials from the lung. It is well known that the insertion of a fiber-optic scope (FOS) requires a special medical procedure as well as the special preparation of a patient since the insertion of a fiber-optic scope (FOS) has the risk of perforating the lung thus causing a hemorrhage. Accordingly, the only specially trained physicians are able to insert a fiber-optic scope (FOS) into the lung of a patient. Since the insertion of a fiber-optic scope (FOS) into the lung of a patient is a specialized procedure, fiber-optic scope (FOS) is not suitable for mechanically cleaning an air passage.

U.S. Pat. No. 4,244,362 to Anderson describes a means for directing an endotracheal tube (ETT) through the larynx and into the trachea. Since the insertion of an endotracheal tube (ETT) through the larynx and into the trachea is a very delicate technique, the device incorporates a magnetic tip to guide the endotracheal tube (ETT) into the trachea by means of a magnet disposed outside of the patient.

Although the aforementioned devices have contributed to the prior art, none of the aforementioned devices considered the problems of (1) maintaining both a constant suction and a constant supply of oxygen to the patient, (2) providing a mechanical dislodging of thick and tenacious material from the walls of the bronchi in the lung and (3) positioning the suction down stream from the flow of the oxygen enabling the oxygen stream to assist in the removal of the material from the walls of the bronchi in the lung.

Therefore, it is an object of the present invention to overcome the disadvantages associated with the alternate use of a single tube withdrawing the solid or the fluid material from the lungs of the patient or for supplying the patient with oxygen for respiration.

Another object of the invention is to provide an improved device for maintaining both a constant suction and a constant supply of oxygen to the patient, and for providing a mechanical dislodging of thick and tenacious material from the walls of the bronchi in the lung.

Another object of the invention is to provide an improved device for removing material from the respiratory tract.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved method and apparatus relating to a multi-lumen catheter which may be inserted into a lung through the trachea, by way of either an endotracheal tube (ETT) or tracheostomy. The multi-lumen catheter is directed to a selected bronchus in the lung.

The multi-lumen catheter suction tube having a first end a second end with a suction tube lumen extending therebetween. The suction tube defines a suction tube opening proximate the second end of the suction tube. An oxygen tube comprises a first end a second end with an oxygen tube lumen extending therebetween. The oxygen tube defines an oxygen tube opening proximate the second end of the oxygen tube. An engaging means is interposed between the suction tube opening and the oxygen tube opening for engaging a surface in the lung. The first end of the suction tube is connected to a source of vacuum for conveying material out of the lung by suction whereas the first end of the oxygen tube is connected to a source of oxygen for simultaneously conveying oxygen into the lung.

In a specific embodiment of the invention, the oxygen tube is helically formed within and secured to the suction tube lumen. The oxygen tube comprises a plurality of oxygen tube openings including an end wall opening being disposed in the second end of the oxygen tube and a sidewall opening being disposed in a sidewall of the oxygen tube.

The engaging means comprises an inflatable balloon secured relative to the suction tube with an inflation tube having a first and a second end with an inflation tube lumen extending therebetween. The inflation tube defines an inflation tube opening proximate the second end of the inflation tube. The first end of the inflation tube is connected to a source of gas pressure for inflating the balloon. In one embodiment of the invention, the inflation tube is disposed within a sidewall of the suction tube.

In use, the multi-lumen catheter is directed to a selected bronchus and inserted as far as desired into the bronchial cavity. When the multi-tubed catheter is in place, the balloon is inflated so that the balloon contacts the sidewall of the bronchus and a forms a seal between the sidewall of the bronchus and the balloon to isolate oxygen tube opening from the suction tube openings. The multi-lumen catheter may be left in place or, if required, pulled to mechanically remove thick and tenacious secretions from the bronchus and trachea by the scraping action of the balloon against the bronchial sidewall. Once these secretions are mechanically dislodged, the secretions are removed from the lung through the suction tube.

While removal of material from the lung is taking place, oxygen is being continuously supplied to the patient through the oxygen tube opening. Accordingly, suction and ventilation of the patient occur simultaneously through the use of the present invention.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 3 is a longitudinal cross-section of the improved multi-tubed catheter of the present invention;

FIG. 4 is a cross-sectional view along line 4—4 of FIG. 3;

FIG. 5 is a cross-sectional view along line 5—5 of FIG. 3;

FIG. 6 is a cross-sectional view along line 6—6 of FIG. 3;

FIG. 7 is a cross-sectional view along line 7—7 of FIG. 3;

Similar reference characters refer to similar part throughout the several Figures of the drawings.

DETAILED DISCUSSION

Figure 1:
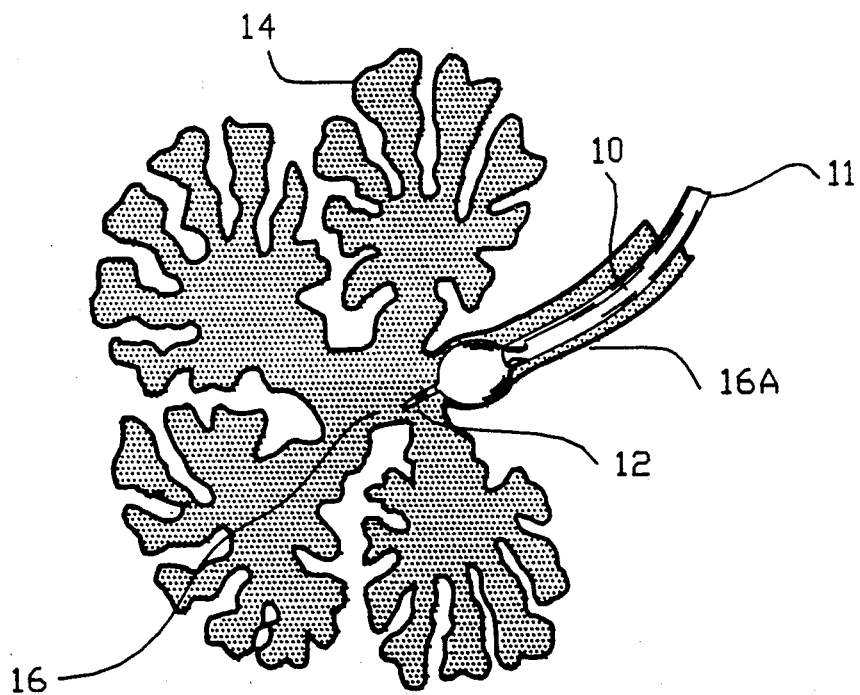
FIG. 1 is a internal view of the improved multi-tubed catheter of the present invention in place in a bronchus of a lung.

FIG. 1 illustrates a multi-tubed catheter 10 of the present invention having a proximal end 11 and a distal end 12. The multi-tubed catheter 10 is shown with the distal end 12 disposed within a cavity of a lung 14 and specifically the middle lobe bronchus 16 of the right lung 14. The multi-tubed catheter 10 is passed into the trachea 18 through an endotracheal tube, a tracheostomy or other means (not shown) which should be wellknown known to those skilled in the art.

Figure 2:
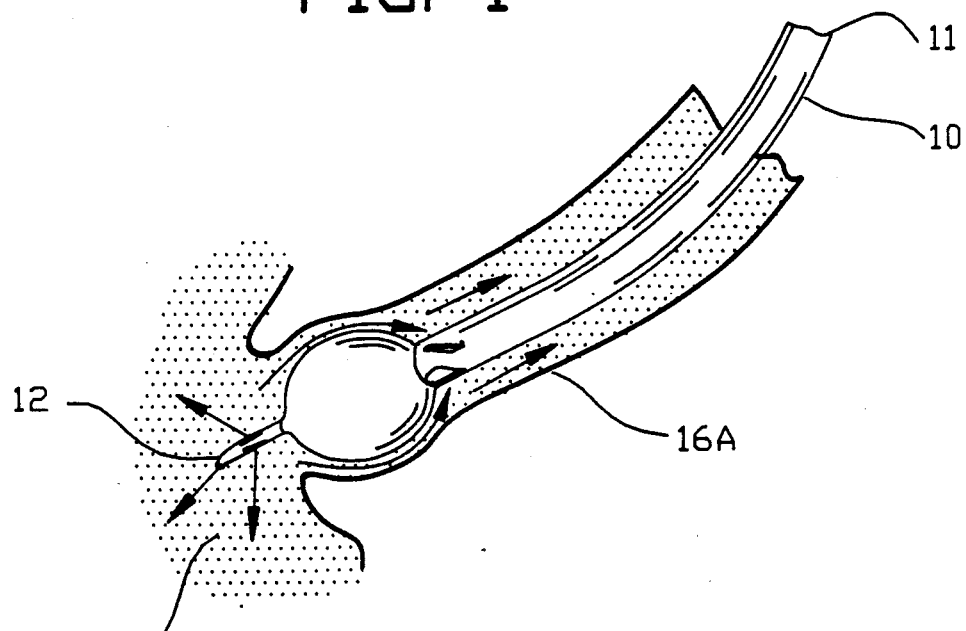
FIG. 2 is an enlarged view of a portion of FIG. 1.

FIG. 2 is an enlarged view of the multi-tubed catheter 10 in operation within the middle lobe bronchus 16 of the right lung 14 which operation will be described in greater detail hereinafter.

FIG. 3 is a longitudinal cross-sectional view of the multitubed catheter 10 with FIGS. 4-7 being various sectional views along the longitudinal length of the multi-tubed catheter 10. The multi-tubed catheter 10 comprises a suction tube 20 having a first end 21 and a second end 22. The suction tube 20 is constructed of a flexible tubular material having a sidewall 23 having an outside surface 23A and an inside surface 23B defining a suction tube lumen 24. The first end 21 of the suction tube 20 is adapted to be connected to a source of vacuum (not shown). The second end 22 of the suction tube 20 comprises an end wall 25. A plurality of suction tube openings 27 are disposed in the sidewall 23 proximate the second end 22 of the suction tube 20. Reference marks 29 are positioned on the outside surface 23A of the suction tube 20 for indication the depth of insertion into the lung 14 of the multi-tubed catheter 10.

The suction tube is preferably constructed of a flexible synthetic material similar to the materials used for conventional catheters and the like. When the first end 21 of the suction tube 20 is connected to a source of vacuum (not shown) a suction is produced at the suction tube openings 27 for removing material therethrough.

An oxygen tube 30 comprises a first end 31 and a second end 32 and is shaped in the form of a helix and is disposed within the suction tube lumen 24 of the suction tube 20. The oxygen tube 31 comprises a sidewall 33 having an outside surface 33A and an inside surface 33B defining an oxygen tube lumen 34 terminating in a coude tip 35. The outside surface 33A of the sidewall 33 of the oxygen tube 30 is secured to an inside surface 23B of the sidewall 23 of the suction tube by suitable means as should be well known to those skilled in the art.

An oxygen tube end opening 36 is defined in the coude tip 35. In addition, oxygen tube sidewall openings 37 are defined in the sidewall 33 of the oxygen tube 30. The coude tip 35 comprises a plurality of openings including the end opening 36 and the sidewall openings 37 in the event that one of the end wall opening 36 or the sidewall openings 37 becomes blocked The coude tip 35 is preferably bent at 38 at an angle of approximately twenty degrees from a longitudinal axis of multi-tubed catheter 10 for directing the insertion of the multi-tubed catheter 10 through a main bronchus into a selected lung cavity for treatment. The first end 31 of the oxygen tube 30 is adapted to be connected to a source of oxygen (not shown) for enabling the flow of oxygen from the oxygen end wall opening 36 and sidewall openings 37 into the lung 14 of the patient.

An inflation tube 40 extends between a first end 41 and a second end 42 and is shown disposed within the sidewall 23 of the suction tube 20. The inflation tube 40 includes an inflation tube sidewall 43 defining an inflation tube lumen 44. The first end 41 is adapted to be connected to a source of pressurized gas (not shown). The second end 42 of the inflation tube 40 includes an end wall 45 and a sidewall aperture 47. The sidewall aperture 47 of the inflation tube 40 communicates with a balloon 50 for inflating the balloon 50 upon the application of a pressurized gas at the first end 41 of the inflation tube 40. The balloon 50 provides a means for engaging a sidewall 16A of the bronchus 16.

In the preferred embodiment of the invention, the suction tube 20 and the inflation tube 40 are formed substantially as a single tube wherein the inflation tube 40 is disposed within the sidewall 23 of suction tube 20. However, the inflation tube 40 may also be a separate tube disposed secured to the outside surface 23A or the inside surface 23B of the sidewall 23 of the suction tube 20 by suitable means as should be well known to those skilled in the art. In an alternate form of the invention, the inflation tube 40 is eliminated and the balloon 50 is inflated through an aperture (not shown) in the sidewall 33 of the oxygen tube 30 position internal the balloon 50.

The balloon 50 is formed of a lightweight, flexible material and forms a first seal 51 with the second end 22 of the suction tube 20 and forms a second seal 52 with the oxygen tube 30. Upon the application of a gas pressure at the first end 41 of the inflation tube 40, the balloon 50 will inflate as shown in FIG. 3. The effective diameter of the balloon 50 may be varied in response to an magnitude of the pressurized air applied at the first end 41 of the inflation tube 40.

The multi-tubed catheter 10 comprises the suction tube 20, the oxygen tube 30, the inflation tube 40 and the balloon 50. The suction tube 20 is adapted to convey material out of the lung by means of suction. The oxygen tube 30 is adapted to provide pure oxygen or an oxygen-rich gas such as humidified oxygen to the patient. The inflation tube 40 is adapted to inflate the balloon 50 for separating the suction of the suction tube 20 from the flow of oxygen or an oxygen-rich gas to the patient of the oxygen tube 30.

Figure 8:
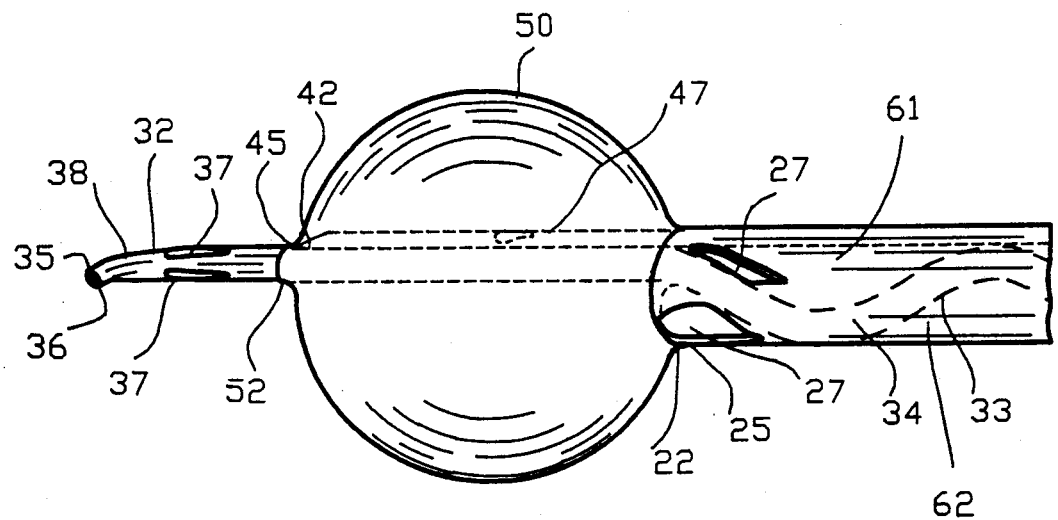
FIG. 8 is an enlarged elevational view of the front of the improved multi-tubed catheter of the present invention.
Figure 9:
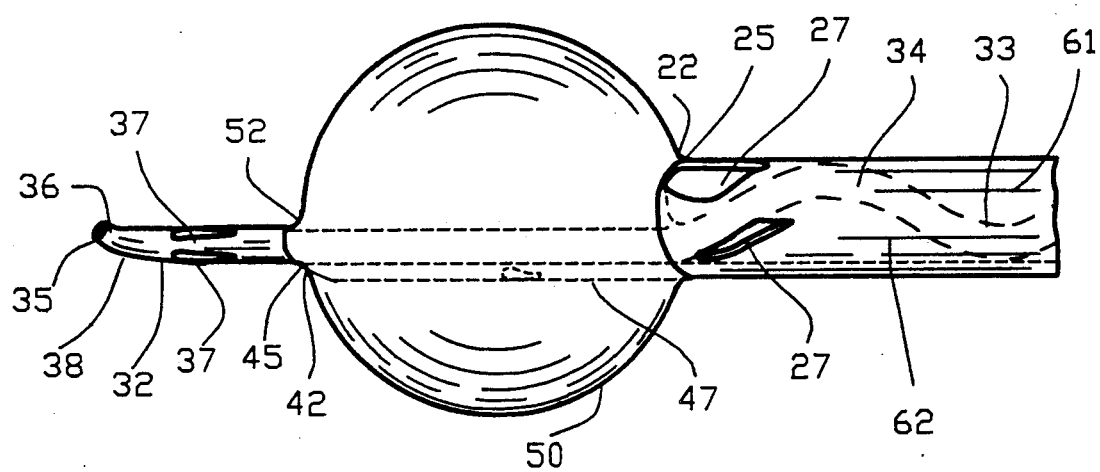
FIG. 9 is an enlarged elevational view of the back of the improved multi-tubed catheter of the present invention.

The oxygen tube 30 forms a first helical path 61 for the flow of the oxygen from the first end 31 to the second end 32. The suction tube openings 27 are preferably of a teardrop-shape and are disposed on a front and back side of the suction tube 20 as shown in FIGS. 8 and 9. The suction tube openings 27 are also formed to be between the helix formed by the oxygen tube 30. Accordingly, the flow of air from the suction tube openings 27 through the suction tube 20 will follow a second helical path 62 formed between the outside surface 33A of the sidewall 33 of the oxygen tube 30 and the inside surface 23B of the sidewall 23 of the suction tube 20. A solid or a fluid material such as mucus which travels up the suction tube 12 will similarly travel through the suction tube 20 along the second helical path 62. Since the second helical path 62 is counter-rotating relative to the first helical path 61, there is substantially no resultant torque produced on the multi-tubed catheter 10 due to the flow of gases though the suction tube 20 and the oxygen tube 30. In addition, since the suction tube 20 comprises two opposed suction tube openings 27 as shown in FIGS. 8 and 9, there is no unbalanced torque or force produced by the air flow through the suction tube openings 27 into the suction tube 20. It is believed that the second helical path 62 also prevent the blockage of the suction tube 20 and make the removal of material more efficient.

The multi-tubed catheter of the present invention is utilized in the following way. Humidified 100% oxygen or similar gas is introduced under pressure into oxygen tube 30. The distal end 12 of the multi-tubed catheter 10 is passed through an endotracheal tube (ETT), a tracheostomy, or other means through the trachea 18 and directed by means of the coude tip 35 into a selected bronchus 16 of the lung 14. While the multi-tubed catheter 10 is inserted, the balloon 50 is uninflated. The coude tip 35 is lodged in the bronchus 16. Preferably, coude tip 35 should be lodged as far as possible into the lung 14. The user may gauge the depth of penetration into the bronchus 16 by means of the reference marks 29. Generally, for an adult, a depth of 400 mm is sufficient; preferably, a length of 100 mm of the unitary portion of the multi-tubed catheter 10 should remain outside of the body of the patient.

When the multi-tubed catheter 10 is fully inserted, a small amount of pressurized gas such as air is introduced into the first end 41 of the inflation tube 50 by means such as a lockable syringe or the like. The pressurized gas will cause the diameter of balloon 50 to expand so that balloon 50 will engage the sidewall 16A of the bronchus 16. The balloon 50 may be designed to have a maximum diameter of between 3.0 mm. and 20.0 mm depending on the size of the patient or lung cavity to be treated. The balloon 18 will generally be fully inflated with less than 10.0 cc. of a gas such as air.

A suction of 200–600 mm Hg is applied to the first end 21 of the suction tube 20. The suction may be controlled by suction regulator (not shown) such as "Luer lock" which should be well known to those skilled in the art. Suction may be applied for periods in excess of 15 seconds.

When the balloon 50 is in contact with the sidewall 16A of the bronchus 16, multi-tubed catheter 10 can be used to physically dislodge thick and tenacious secretions from the bronchus by slightly withdrawing the multi-tubed catheter 10 so that the balloon 50 may mechanically remove secretions from the sidewall 16A of the bronchus 16.

With oxygen being forced into the lung 14 through oxygen tube 30, and suction being applied through suction tube 20, the multi-tubed catheter 10 may be gradually and totally pulled out of the bronchus 14 to scraping any thick and tenacious secretions from the sidewall 16A of the bronchus 16. As the balloon 50 passes through wider cross-sections of bronchus 16, the balloon 50 is further inflated to maintain contact between balloon 50 and the sidewall 16A of the bronchus 16. As the secretions are dislodged by the motion of balloon 50, the dislodged matter is drawn through suction tube openings 27 in suction tube 20 and is conducted out of the multi-tubed catheter 10 through cavity suction tube lumen 24.

Simultaneously, oxygen entering the lung 14 through oxygen tube 30 and coude tip 35 is aerating the newly-clean bronchi. In addition to its function in dislodging secretions from the sidewall 16A of the bronchus 16, the balloon 50 may serve a second function as a partial blockage against for the escape of oxygen from the bronchus 16. This blockage will result in a high oxygen pressure within the lung 14. This is desirable because oxygen exchanges into lung tissue more efficiently at this higher pressure. If, for any reason, suction must suddenly be stopped, the balloon 50 may be deflated rapidly allowing the multi-tubed catheter 10 to be removed quickly in a conventional manner.

In a preferred embodiment of the invention, the source of vacuum (not shown) connected to the first end 21 of the suction tube 20, the source of oxygen (not shown) connected to the first end 31 of the oxygen tube 30, and the source of pressurized gas connected to the first end 41 of the inflation tube 50 are regulated and appropriately balanced. If the pressure applied to the balloon 50 is greater than the pressure applied to the oxygen tube 30, then a distal pressured oxygen known in the art as a (CPAP) is created from the occluding balloon and the oxygen emanating from the oxygen tube will be flooded into the lungs. If the pressure applied to the balloon 50 is less than the pressure applied to the oxygen tube 30, then the pressure of the oxygen from the oxygen tube 30 will deflate the balloon 50 enabling the flow of oxygen around the outside of the balloon 50. The flow of oxygen around the outside of the balloon 50 will convey any material to the suction tube opening 37.

The present invention provides many advantage over the prior art. The present invention physically dislodges material in a more effective way than is possible with the simple single tube of the prior art. The balloon 50 starts deep in a bronchial cavity, and as the balloon 50 is pulled out, the balloon 50 scrapes the mucus from the sidewall 16A of the bronchus 16 until all the mucus is drawn out. This methodical suctioning is more efficient than that of previous devices because, instead of suctioning just what is near the suction tip of an ordinary catheter, an entire branch of the bronchotracheal tree can be systematically cleaned.

In addition, once the balloon 50 is inflated, a substantial seal is formed between the oxygen entering the lung through coude tip 35 and the suction through suction tube openings 27. Because of the seal, there is a relatively high pressure of oxygen against the alveoli, for a more efficient oxygen exchange into the lung tissue. Also, the combination of outward pressure of oxygen and suction through the suction tube will tend to cause mucus near the coude tip 35 to be pushed around the balloon 50 and into the suction tube openings 27 of suction tube 20, thus further enhancing the efficiency of material removal.

Moreover, the combination of oxygen pressure into the lung and suction out of the lung enables the user of relatively high levels of suction, as high as 600 mm Hg, without damaging tissue in the lung. Higher levels of suction enable greater efficiency in removing materials from the lungs.

The multi-tubed catheter 10 of the present invention is generally made of polyvinyl chloride (PVC), though other types of rubber of plastic could be used. The balloon 50 may be constructed of a flexible plastic material such as silicone or the like. In one embodiment of the invention, the oxygen tube 30 is constructed of a sightly more rigid material relative to the suction tube 20. The sightly more rigid oxygen tube 30 will inhibit the twisting of the multi-tubed catheter 10. In addition, the sightly more rigid oxygen tube 30 will prevent the collapse of the suction tube 20 in the event that the suction tube opening 37 are block by the material. It is preferable that the multi-tubed catheter 10 be of a material that will withstand transportation and changes in temperature.

The multi-tubed catheter 10 can be designed within a wide range of dimensions for use in specific needs, such as with infants. The overall length may be between 300–600 mm, and the outside diameter of the suction tube 20 of the multi-tube catheter 10 may be between 2–7 mm. Generally, however, the relative diameters of the suction tube 20, the oxygen tube 30 and the inflation tube 40 should be: suction tube 20–50% of the total external diameter; oxygen tube 30–30% of the external diameter; and inflation tube 40–20% of the external diameter. The maximum diameter of the balloon 50 may vary from between 3-20 mm.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. Apparatus for removing material from a bronchial cavity of a lung and for simultaneously aerating the lung, comprising:
    a suction tube having a first end and a second end with a suction tube lumen extending therebetween;
    said suction tube being sufficiently flexible and sufficiently small in diameter to enter the bronchial cavity of the lung;
    said suction tube defining a plurality of suction tube openings proximate said second end of said suction tube;
    an oxygen tube having a first end a second end with an oxygen tube lumen extending therebetween;
    said oxygen tube being disposed within said suction tube lumen and being secured to said suction tube lumen;
    said oxygen tube defining an oxygen tube opening proximate said second end of said oxygen tube;
    an inflatable balloon secured to said suction tube between said suction tube opening and said oxygen tube opening for engaging a surface in the lung;
    said inflatable balloon being adapted to physically dislodge tenacious material from the surface in the lung upon a movement of said inflatable balloon relative to the surface in the lung;
    means for connecting said first end of said suction tube to a source of vacuum for conveying material out of the lung by suction;
    means for connecting said first end of said oxygen tube to a source of oxygen for simultaneously conveying oxygen into the lung; and
    each of said plurality of suction tube openings has a general shape of a teardrop for facilitating the entry of tenacious material from the surface of the lung.

2. Apparatus for removing material as set forth in claim 1, wherein said oxygen tube comprises a plurality of oxygen tube openings;
    an end wall opening of said plurality of oxygen tube openings being disposed in said second end of said oxygen tube; and
    a sidewall opening of said plurality of oxygen tube openings being disposed in a sidewall of said oxygen tube.

3. Apparatus for removing material as set forth in claim 1, including an inflation tube having a first and a second end with an inflation tube lumen extending therebetween;
    said inflation tube defining an inflation tube opening proximate said second end of said inflation tube; and
    means for connecting said first end of said inflation tube to a source of gas pressure for inflating said balloon.

4. Apparatus for removing material as set forth in claim 3, wherein said inflation tube is disposed generally parallel to said suction tube.

5. Apparatus for removing material as set forth in claim 3, wherein said inflation tube is disposed within said suction tube.

6. Apparatus for removing material as set forth in claim 3, wherein said inflation tube is disposed within a sidewall of said suction tube.

7. Apparatus for removing material from a bronchial cavity of a lung and for simultaneously aerating the lung, comprising:
    a suction tube having a first end and a second end with a suction tube lumen extending therebetween;
    said suction tube being sufficiently flexible and sufficiently small in diameter to enter the bronchial cavity of the lung;
    said suction tube defining a plurality of suction tube openings proximate said second end of said suction tube;
    an oxygen tube having a first end a second end with an oxygen tube lumen extending therebetween;
    said oxygen tube being disposed within said suction tube lumen and being secured to said suction tube lumen;
    said oxygen tube defining an oxygen tube opening proximate said second end of said oxygen tube;
    an inflatable balloon secured to said suction tube between said suction tube opening and said oxygen tube opening for engaging a surface in the lung;
    said inflatable balloon being adapted to physically dislodge tenacious material from the surface in the lung upon a movement of said inflatable balloon relative to the surface in the lung;
    means for connecting said first end of said suction tube to a source of vacuum for conveying material out of the lung by suction;
    means for connecting said first end of said oxygen tube to a source of oxygen for simultaneously conveying oxygen into the lung;
    said oxygen tube is helically formed within said suction tube lumen; and
    said oxygen tube being secured to said suction tube lumen for forming a first helical path for the flow of the oxygen within said oxygen tube and for forming a second helical path with said suction tube lumen for said suction tube.

8. Apparatus for removing material as set forth in claim 7, wherein said oxygen tube comprises a plurality of oxygen tube openings;
    an end wall opening of said plurality of oxygen tube openings being disposed in said second end of said oxygen tube; and
    a sidewall opening of said plurality of oxygen tube openings being disposed in a sidewall of said oxygen tube.

9. Apparatus for removing material as set forth in claim 7, including an inflation tube having a first and a second end with an inflation tube lumen extending therebetween;
    said inflation tube defining an inflation tube opening proximate said second end of said inflation tube; and
    means for connecting said first end of said inflation tube to a source of gas pressure for inflating said balloon.

10. Apparatus for removing material as set forth in claim 9, wherein said inflation tube is disposed generally parallel to said suction tube.

11. Apparatus for removing material as set forth in claim 9, wherein said inflation tube is disposed within said suction tube.

12. Apparatus for removing material as set forth in claim 9, wherein said inflation tube is disposed within a sidewall of said suction tube.

13. A method for removing material from a lung and for simultaneously aerating the lung with a multi-tubed catheter having a suction tube and an oxygen tube with an inflatable balloon interposed therebetween, comprising the steps of:
  inserting the multi-tubed catheter into the lung;
  connecting the oxygen tube to a source of oxygen for conveying oxygen into the lung;
  inflating the balloon to engage a surface in the lung;
  at least partially withdrawing the multi-tubed catheter from the lung to dislodge material from the lung; and
  connecting the suction tube to a source of vacuum for conveying material out of the lung by suction.

* * * * *